(12) United States Patent
Hattori

(10) Patent No.: US 6,268,395 B1
(45) Date of Patent: Jul. 31, 2001

(54) PHORBOL DERIVATIVES HAVING ANTIVIRUS ACTIVITY

(75) Inventor: Masao Hattori, Toyama (JP)

(73) Assignee: Lead Chemical Co., Ltd., Toyama (JP)

( * ) Notice: Subject to any disclaimer, the term of this patent is extended or adjusted under 35 U.S.C. 154(b) by 0 days.

(21) Appl. No.: 09/563,499

(22) Filed: May 3, 2000

(30) Foreign Application Priority Data

Nov. 11, 1999 (JP) .................................................. 11-320867

(51) Int. Cl.⁷ .................................................. A61K 31/215
(52) U.S. Cl. ............................................ 514/530; 554/229
(58) Field of Search ............................... 554/229; 514/530

(56) References Cited

PUBLICATIONS

Che, Plants as a source of potential antiviral agents, Economic and Medicinial Plant Research, vol. 5, (1991).

Schinazi, Progress in the Development of Natural Products for Human Immunodefieciency Viruses Infections, Natural Products as Antiviral Agents, pp. 1–29, (1992).

Nasr et al., Structure–Activity Correlations of Natural Products with Anti–HIV Activity, Natural Products as Antiviral Antviral Agents, pp. 31–56, (1992).

El–Mekkawy et al., Anti–HIV and Anti–HIV–1–Protease Substances from *Ganoderma Lucidum,* Phytochemistry, pp. 1651–1657, (1998).

El–Mekkawy et al., Inhibitory Effects of Egyptian Folk Medicines on Human Immunodeficiency Virus (HIV) Reverse Transcriptase, Chem. Pharm. Bull, pp. 641–648, (1995).

Ng et al., Anti–Human Immunodefieciency Virus (Anti–HIV) Natural Products with Special Emphasis on HIV Reverse Transcriptase Inhibitors, Life Sciences, pp. 933–949, (1997).

Kusumoto et al., Search for Anti–HIV Agents Among Traditional Medicines, Pharmacological Research on Traditional Herval Medicines, pp. 219–235, (1999).

*Primary Examiner*—Deborah D. Carr
(74) *Attorney, Agent, or Firm*—Oliff & Berridge, PLC

(57) ABSTRACT

An antiviral agent comprising as an active ingredient a phorbol derivative of formula (I):

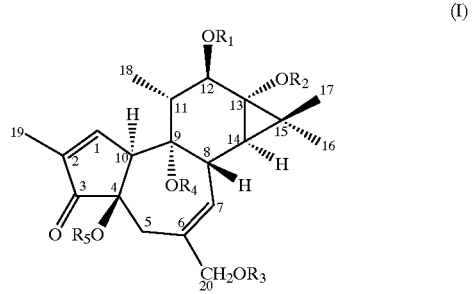

(wherein $R_1$, $R_2$, $R_3$, $R_4$, and $R_5$, independently one another, represent a hydrogen atom, an aliphatic carboxylic acid residue, or an aromatic carboxylic acid residue)

having a ratio $r=CC_0/IC_{100}$, i.e., ratio of concentration $CC_0$ at which survival of MT-4 cells is decreased upon cell proliferation tests to concentration $IC_{100}$ at which HIV-1-induced cytopathic effect (CPE) on MT-4 cells is inhibited by 100%, of 2 or more and having a protein kinase C(PKC) activation of 30% or less at a concentration of 10 ng/mL.

The agent is useful as an anti-HIV agent.

3 Claims, No Drawings

PHORBOL DERIVATIVES HAVING ANTIVIRUS ACTIVITY

BACKGROUND OF THE INVENTION

1. Field of the Invention

The present invention relates to phorbol derivatives having antiviral activity, more particularly to an antiviral agent effective against virus such as human immunodeficiency virus (HIV) containing a phorbol derivative as an active ingredient, and to novel phorbol derivatives.

2. Description of the Related Art

Since the discovery of human immunodeficiency virus, the causative agent of the acquired immunodeficiency syndrome (AIDS), significant progress has been made towards the development of effective anti-HIV drugs and recently considerable progress has been made in this field. In the research and development of AIDS therapeutics, research for natural substances having anti-HIV activity has been made besides research and development of novel chemical drugs. For example, a variety of compounds having various chemical structures derived from plants have been reported to be effective in inhibiting the replication of HIV-1 or its essential enzymes (cf. for example, Che, 1991; Schinazi, 1992; Nasr, Cradock & Johnson, 1992; El-Mekkawy et al., 1995; El-Mekkawy, Meselhy, Kusumoto, Kadota, Hattori, Namba, 1998; Ng, Huang, Fong & Yeung, 1997; Kusumoto & Hattori, 1999).

Plant-derived bioactive substances are relatively easily available from plants. There are many plants which are used as materials for Japanese-Chinese medicines or folk medicines over the world so that many pieces of information on bioactivity have accumulated and the plants are greatly expected to be also potent anti-HIV drugs.

However, none of the plant-derived compounds that have anti-HIV effects is sufficient in its activity. Since some of the above-mentioned plant-derived substances show deleterious side effects such as cytotoxicity or carcinogenicity, it is very difficult to select most suitable antiviral agents such as, for example, anti-HIV drugs, taking into consideration both useful bioactivity and harmful bioactivity. Therefore, it has been keenly desired to find plant-derived bioactive substances having high antiviral effects (for example, anti-HIV effects) and having less deleterious side effects and develop effective antiviral agents, for example anti-HIV agents, based thereon.

SUMMARY OF THE INVENTION

The present invention has been made with view to solving the above-described defects of the prior art.

It is an object of the present invention to provide an antiviral agent (for example anti-HIV agent) having higher antiviral effects and less deleterious side effects as compared with conventionally known antiviral agents.

Another object of the present invention is to provide a novel substance that can be used as an active ingredient for the antiviral agent.

The present inventor has conducted extensive research for the screening of about several hundreds to about one thousand kinds of Japanese-Chinese medicines and plant-derived natural raw materials for their antiviral activities. As a result, he has found that the components contained in the seeds of Croton tiglium, particularly phorbol derivatives, have potent inhibitory effect against proliferation of AIDS virus, thus having achieved the present invention.

Accordingly, in a first aspect, the present invention relates to an antiviral agent comprising as an active ingredient a phorbol derivative of formula (I):

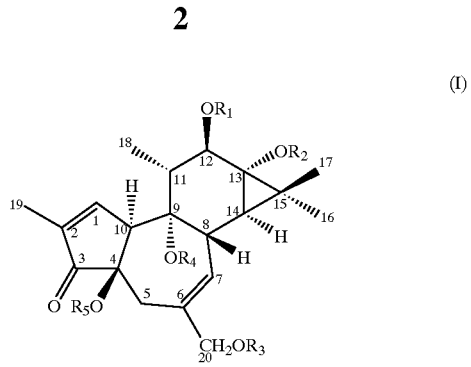

(wherein $R_1$, $R_2$, $R_3$, $R_4$, and $R_5$, independently one another, represent a hydrogen atom, an aliphatic carboxylic acid residue, or an aromatic carboxylic acid residue)

having a ratio $r = CC_0/IC_{100}$, i.e., ratio of concentration $CC_0$ at which survival of MT-4 cells is decreased upon cell proliferation tests to concentration $IC_{100}$ at which HIV-1-induced cytopathic effect(CPE) on MT-4 cells is inhibited by 100%, of 2 or more and having a protein kinase C(PKC) activation of 30% or less at a concentration of 10 ng/mL.

In a second aspect, the present invention relates to an antiviral agent comprising as an active ingredient a phorbol derivative of formula (II):

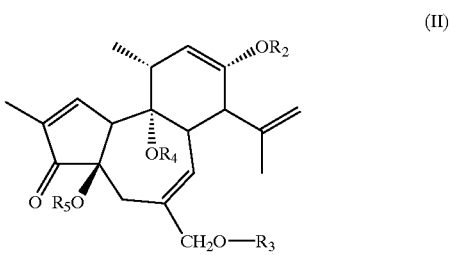

(wherein $R_1$, $R_2$, $R_3$, $R_4$, and $R_5$, independently one another, represent a hydrogen atom, an aliphatic carboxylic acid residue, or an aromatic carboxylic acid residue)

having a ratio $r = CC_0/IC_{100}$, i.e., ratio of concentration $CC_0$ at which survival of MT-4 cells is decreased upon cell proliferation tests to concentration $IC_{100}$ at which HIV-1-induced cytopathic effect(CPE) on MT-4 cells is inhibited by 100%, of 2 or more and having a protein kinase C(PKC) activation of 30% or less at a concentration of 10 ng/mL.

In a third aspect, the present invention relates to a phorbol derivative of formula (I):

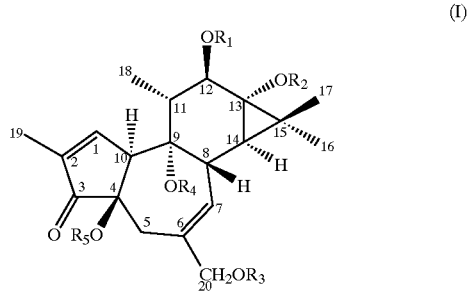

(wherein
$R_1$, $R_4$, and $R_5$ represent each a hydrogen atom, $R_2$ represents an acetyl group, $R_3$ represents a linoleic acid residue, or $R_1$, $R_4$, and $R_5$ represent each a hydrogen atom, $R_2$ represents a tigloyl group, $R_3$ represents a linoleic acid residue, or $R_1$ represents an acetyl group, $R_2$ represents a tigloyl group, $R_3$, $R_4$, and $R_5$ represent each a hydrogen atom, or $R_1$ represents a decanoyl group, $R_2$ represents a 2-methyllactic acid residue, $R_3$, $R_4$, and $R_5$ represent each a hydrogen atom, or $R_1$ represents a tigloyl group, $R_2$ represents a decanoyl group, $R_3$, $R_4$, and $R_5$ represent each a hydrogen atom).

DETAILED DESCRIPTION OF THE INVENTION

Hereinafter, the present invention will be described in detail. For the convenience's sake, the following explanation will be focused mainly on HIV.

In the course of search for anti-HIV-1 agents from natural products, a number of extracts of plants used in Egyptian folk medicine were evaluated for possible anti-HIV properties, and it revealed that the methanol and water extracts of the seeds of Croton tiglium significantly inhibited the infectivity and HIV-1-induced cytopathic effect(CPE) on MT-4 cells at concentrations ($IC_{50}$ values of 0.025 and 2.0 $\mu$g/mL, respectively) below the cell toxic concentration (selectivity indices of 34.4 and 50.0, respectively) (Kawahata, Otake, Mori, Morimoto, Ueba, Kusumoto et al., 1996). Croton tiglium belongs to the family Euphorbiaceae and is known to contain tigliane phorbol esters. These compounds have been shown to be responsible for eliciting a remarkable range of biochemical effects on a variety of biological systems (cf. Evans & Taylor, 1983; Evans & Soper, 1978; De Chaffoy de Courcelles, Roevens & van Belle, 1984; Hecker, 1978; Blumberg, 1980; Blumberg 1981; Blumberg, 1988; Kupchan, Uchida, Branfman, Daily & Yu-Fei, 1979; Gustafson, Cardellina, II, McMahon, Gulakowski, Ishitoya, Szallasi et al., 1992; Gschwendt & Hecker, 1974).

That is, these include tumor promotion, cell proliferation, platelet aggregation, antitumor and anti-HIV-1 effects. Much of what is known about how these effects are transmitted inside cells come from the study of tumor promoting and platelet aggregating phorbol esters like 12-O-tetradecanoylphorbol-13-acetate (Compound 8, TPA) . Although the ability of these compounds to promote tumors presents one potential limitation to their utility, it should be stressed that there are many phorbol esters that exert profound effects without being tumor promoters.

12-O-tigloylphorbol-13-decanoate isolated from croton oil demonstrated antileukemic activity against the P-388 leukemia in mice (Kupchan et al., 1976). 12-Deoxyphorbol-13-acetate having an anti-HIV activity was isolated from a Samoan plant, Homolanthus nutans (Gustafson et al., 1992). Although structurally belonging to the phorbol esters, it does not exhibit a tumor promoting effect, while 12-deoxyphorbol-13-tetradeconoate isolated from Euphorbia triangularis possesses the same tumor promoting activity as TPA (Geschwendt et al., 1974). These findings suggested that the difference among tumor promoting, antitumor and anti-HIV-1 effects of an ester is associated with the specific structure of the entire molecule, and that particular structural features are necessary for phorbol esters to provoke these diverse effects.

It has been reported that these compounds interact with and activate protein kinase C(PKC), and that their tumor promoting and HIV-1 inhibitory effects were mediated through their direct activation of PKC (cf., for example, Nishizuka, 1984; Nishizuka, 1986; Nishizuka, 1988; Bell, 1986; Weinstain, 1988, Rahmsdorf & Herrlich, 1990; Raineri, Simsiman & Boutwell, 1973; Castagna, Takai, Kaikuchi, Sano, Kikkawa & Nishizuka, 1982; Chowdhury, Koyagi, Kobayashi, Hamamato, Yoshiyama, Yoshida et al., 1990; Keenan, Long & Kelleher, 1997).

The present inventor has isolated 8 phorbol diesters and carried out structural modifications of the isolated compounds. Also, the present inventor has prepared other phorbol derivatives and investigated their anti-HIV activity and activation effect of PKC in order to evaluate their usefulness as antiviral agents. Analysis of the structure-activity relationships of these compounds has led to the structural features that gives a lesser degree of activation of PKC and that is necessary for selective inhibition of HIV-1-induced CPE. The phorbol derivatives that can be used in the present invention provide structural information, which may guide the further design of various phorbol derivatives having more potent antiviral effects including anti-HIV-1 effect.

In the phorbol derivatives of formula (I), $R_1$, $R_2$, $R_3$, $R_4$, and $R_5$ independently one another, represent within the specified range of groups. The aliphatic carboxylic acid residue or aromatic carboxylic acid residue as used herein mean the moiety of an aliphatic or aromatic carboxylic acid of general formula RCOOH from which OH has been removed, i.e., the moiety RCO and specifically may be, for example, an acetyl group, a benzyl group, a tigloyl group, etc.

The phorbol derivatives of formula (II) wherein $R_2$, $R_3$, $R_4$, and $R_5$ have the same meanings as defined in formula (I), can be derived from the phorbol derivatives of formula (I) and correspond to those derivatives in which three-member cycle portion has been cleaved.

Many of the phorbol derivatives of formulae (I) or (II) have excellent antiviral effects and therefore they can be used as an antiviral agent, for example, as an active ingredient of anti-HIV agents. However, the phorbol derivatives of formula (I) include those having low antiviral effects or having high deleterious side effects and hence they are selected so as to have a certain level or more of antiviral effect according to first selectivity indices of the above-mentioned $r=CC_0/IC_{100}$ being 2 or more and then a certain level or less of deleterious side effects according to second selectivity indices of the above-mentioned protein kinase C(PKC) activation of 30% or less.

As described above, some of the phorbol derivatives have strong tumor promoting effects, so that it is necessary to select phorbol derivatives having strong antiviral effects but having weak deleterious effects such as tumor promoting effects.

EXAMPLES

Hereinafter, the present invention will be described in more detail by examples, which are divided into the parts of "Experiments" and "Results and Discussion". However, the present examples are merely illustrative and should not be construed as being limited thereto.

1. "Experiments"

a) Instrumental analysis

Optical rotations were obtained on a DIP-360 automatic polarimeter (JASCO, Kyoto, Japan). IR spectra were recorded on a FT/IR-230 spectrophotometer (JASCO, Kyoto, Japan). UV spectra were measured with a UV-2200 UV-VIS recording spectrophotometer (Shimadzu, Kyoto, Japan). NMR spectra were obtained on a Varian Unity plus 500 ($^1H$, 500 MHz; $^{13}C$, 125 MHz) spectrometer and chemical shifts (δ) were given relative to tetramethylsilane (TMS). Electron impact(EI) mass spectra were obtained with a JMS-AX 505 HAD spectrometer(JEOL) at an ionization voltage of 70 eV. Atmospheric pressure ionization (API) mass spectra were measured with a PESCIEX API III biomolecular mass analyzer.

b) Chromatography

α) TLC:

Silica gel 60 $F_{254}$ and RP-18$F_{254}$ S plates (Merck, Darmstadt, Germany); and spots were detected under UV light or after spraying with anisaldehyde-$H_2SO_4$ reagent, followed by heating.

β) Column chromatography:

Silica gel 60 (70-230 mesh, Merck), ODS Cosmosil 140 C18-OPN (Nacalai Tesque, Kyoto, Japan).

γ) Medium pressure liquid chromatography (MPLC):

This was performed on a LiChroprep Si 60 column or LiChroprep RP-18 column (A size, Merck, Darmstadt).

δ) Gas chromatography-mass spectra (GC-MS):

These were obtained using a GC-17A gas chromatograph (Shimadzu, Kyoto, Japan) fitted with a DB-1 column [0.25 mm (i.d)×30 mm] (J & W Scientific, USA), coupled to an automass system II benchtop quadruple mass spectrometer (JEOL, Japan) under the following conditions:

Column temperature: 50° C. for 10 minutes and gradient to 250° C. (10° C./min) for 20 minutes;

Injection temperature: 250° C., or isothermal at 30° C. for 30 minutes (for methyl esters of short-chain fatty acids;

Injection temperature: 170° C.;

Carrier gas: He (flow rate at 15mL/min).

c) Test Material

Seeds of Croton tiglium were purchased at Harraz Herbal drug store, Cairo, Egypt and were authenticated by Professor El-Sayed E. Aboutabl, Faculty of Pharmacy, Cairo University, Egypt. A voucher specimen was deposited at the Museum of Materia Medica of Toyama Medical and Pharmaceutical University, Toyama, Japan.

d) Chemicals and Enzymes

Chemicals and enzymes conventionally used in this field of art were used.

e) Isolation of compounds 1 to 8

The air-dried seeds (3 kg) were homogenized with an electric mill and refluxed with methanol (10 liters×3) for 3 hours. The methanol solutions were combined and evaporated under reduced pressure to give 763 g of an oily residue. The residue was suspended in 90% aqueous methanol (7 liters) and extracted with hexane (4 liters×3) and then ether (4 liters×3). The ether solutions were combined and evaporated under reduced pressure to give a resinous residue (150 g). The residue was chromatographed on a column of silica gel (2 kg) After washing with hexane (5 liters), elution was started with hexane-ethyl acetate (9:1→6:4) and then chloroform-methanol (9:1, 8:2, 7:3) to furnish 20 fractions (Fr. 1 to Fr. 20). Column chromatography of Fr. 13 using MPLC (RP-18, methanol-water, 9.5:0.1) afforded 13-O-tigloylphorobol-20-(9Z,12Z-octadecdienoate)(compound 2; 60 mg). Fr. 17 was applied to a column of R-2, which was then eluted with methanol-water (9:1) to obtain two subtractions, Fr. 17-A (683 mg) and 17-B (217 mg). MPLC of Fr. 17-A afforded 13-O-acetylphorbol-20- (9Z, 12Z-octadecadienoate) (Compound 1; 153 mg), while MPLC of Fr. 17-B gave 12-O-decanoylphorbol-13-(2-methylbutryrate) (compound 4; 21 mg) and 12-O-(2-methylburyroyl) phorbol-13-dodecnoate (compound 7; 30 mg). A portion (1 g) of Fr. 18 to 20 was further fractionated by column chromatography (RP-2, methanol-water, 6:4) to give Fractions (I to X). Through MPLC (RP-18) with methanol-water, Fr. III (8:2) gave 12-O-acetylphorbol-13-tigliate (compound 3: 35 mg), Fr. V (9:1) afforded 12-O-acetylphorbol-13-decanoate (compound 6: 74 mg), and Fr. VI gave 12-O-decanoylphorbol-13- (2-methylbutyrate) compound 4; 57 mg). Similarly, upon elution with methanol-acetonitrile (4:6), Fr. IX gave 12-O-tigloylphorbol-13-(2-methylbutyrate) (compound 5; 12 mg) Upon elution with methanol-water (9.4:0.6), Fr. X gave 12-O-decanoylphorbol-13-acette (compound 8; 110 mg). Of the compounds 1 to 8, the compounds 1 to 5 are novel compounds.

f) Preparation of phorbols (compounds 9, 19, and 20)

According to the literature, Fr. 8 to 20 (40 mg) was mixed with a solution of barium hydroxide (2.2% methanol solution, 400/mL) and stirred under an atmosphere of argon for 1 hour at room temperature to obtain a crude phorbol fraction (Mishra, Estensen & Abdel-Monem, 1986; Cairnes, Mirvish, Wallcave, Nagel & Smith, 1981). Column chromatography of the fraction on silica using chloroform-methanol (9.5:0.5, 7:3) and subsequent purification with MPLC (RP-18), methanol-water 4:6) yielded phorbol (compound 9; 537mg), 4α-phorbol (or isophorbol) (comound 19; 185mg) (Hecker, 1966; Tseng et al., 1977; Evans et al., 1973; Hecker et al., 1976) and 4-deoxy-4α-phorbol (compound 20; 10 mg) (Furstenberger & Hecker, 1977).

g) Synthesis of various phorbol derivatives (compounds 10 to 18 and 21 to 24)

In order to undertake structure-activity relationship studies of phorbol esters, I prepared various derivatives based on phorbol (compound 9) and isophorbol (compound 19). Selective hydrolysis of 13-O-acetylphorbol-20-(9Z,12Z-octadecadienoate) (compound 1) with $HClO_4$ afforded 13-O-acetylphorbol (compound 10) (Zayed, Sorg & Hecker, 1984), while treatment of 13-O-acetylphorbol-20-(9Z,12Z-octadecadienoate) (compound 1) with acetic anhydride/ pyridine for 24 hours at room temperature to obtain phorbol-12,13-diacetate-20-linoleate (compound 13). Reaction of the compound 1 with mesyl chloride/pyridine at room temperature for 21 hours gave 13-O-acetylcrotophorbolone-enol-20-linoleate of compound 18 afforded 13-O-acetylcrotophorbolone-enol-20-linoleate (compound 18) (Bartsch et al., 1969). By acetylation, 12-O-decanoylphorbol-13-acetate (compound 8) gave 12-O-tetradecanoylphorbol-13,20-diacetate (compound 14), and isophorbol (compound 19) gave 4α-phorbol-12,13,20-triacetate (compound21) and 4α-phorbol-4,12,13,20-tetraacetate (compound 23) (Hecker, Harle, Schairer, Jacobi, Hoppe & Gassmann, 1968). Acetylation of the compound 9 under the condition of 90° C./1 hour afforded phorbol-12, 13,20-triacetate (compound 11) (Heckeretal., 1965; Heckeret al., 1966). Irradiation of compound21with UV light (254 nm, 5 hours) afforded lumiphorbol-12,13,20-triacetate (compound 24) (Hecker et al., 1968). Reduction of compound 11 with $NaBH_4$ gave 3-deoxo-3β-hydroxyphorbol-12,13,20-triacetate (compound 15) (Hecker et al., 1967). Then, methylation of compound 15 with $Ag_2O/CH_3I$ in DMF at room temperature for 20 hours afforded 4-O-methylphorbol-12,13,20-triacetate (compound 16) (Bartsch et al., 1968). Treatment of the compound 11 with acetic anhydride/p-toluenesulfonic acid resulted in the synthesis of phorbol-4,9,12,13,20-pentaacetate (compound 17) (Hecker et al., 1966). Reaction of the compound 9 with benzoyl chloride/pyridine affordedphorbol-12, 13,20-tribenzoate (compound 12) (Heckeretal., 1966; Crombe et al., 1968). Reaction of the compound 19 with butyryl chloride/pyridine afforded gave 4α-phorbol-4,12,13,20-tributyrate (compound22). Allderivatives prepared were worked up as reported previously and purified by column chromatography on silica gel, followed by MPLC over LiChroprep RP-18.

The names and compound numbers of various phorbol derivatives produced in e) to g) above are shown in Table 1 collectively.

TABLE 1

| Various phorbol derivatives Name of Phorbol Derivative | No. |
|---|---|
| 13-O-Acetylphorbol-20-(9Z,12Z-octadecadienoate) | 1 |
| 13-O-Tigloylphorobol-20-(9Z,12Z-octadecadienoate) | 2 |
| 12-O-Acetylphorbol-13-tigliate | 3 |
| 12-O-Decanoylphorbol-13-(2-methylbutyrate) | 4 |
| 12-O-Tigioylphorbol-13-(2-methylbutyrate) | 5 |
| 12-O-Acetylphorbol-13-decanoate | 6 |
| 12-O-(2-Methylbutyroyl)phorbol-13-dodecanoate | 7 |
| 12-O-Decanoylphorbol-13-acetate | 8 |
| Phorbol | 9 |
| 13-O-Acetylphorbol | 10 |
| Phorbol-12,13,20-triacetate | 11 |
| Phorbol-12,13,20-tribenzoate | 12 |
| Phorbol-12,13-diacetate-20-linoleate | 13 |
| 12-O-Tetradecanoylphorbol-13,20-diacetate | 14 |
| 3-Deoxo-3β-hydroxyphorbol-12,13,20-triacetate | 15 |
| 4-O-Methylphorbol-12,13,20-triacetate | 16 |
| Phorbol-4,9,12,13,20-pentaacetate | 17 |
| 13-O-Acetylcrotophorbolone-enol-20-linoleate | 18 |
| 4α-Phorbol (or isophorbol) | 19 |
| 4-Deoxy-4α-phorbol | 20 |
| 4α-Phorbol-12,13,20-triacetate | 21 |
| 4α-Phorbol-12,13,20-tributyrate | 22 |
| 4α-Phorbol-4,12,13,20-tetraacetate | 23 |
| Lumiphorbol-12,13,20-triacetate | 24 |

The structures and substituents of the phorbol derivatives are shown in Table 2 collectively.

Phorbol derivatives 1 to 17: Compounds of formula (I) above;

Phorbol derivative 18: Compound of formula (II) above;

Phorbol derivatives 19 to 23: Compounds of formula (III):

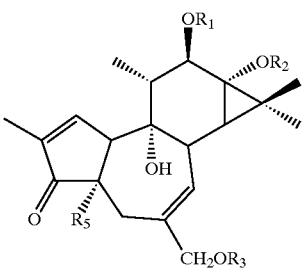

(III)

Phorbol derivative 24: Compound of formula (IV):

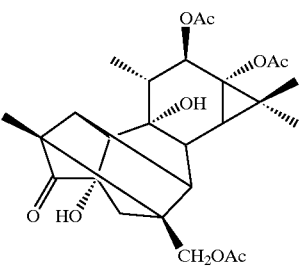

(IV)

TABLE 2

Substituents of various derivatives

| No. | 式 | $R_1$ | $R_2$ | $R_3$ | $R_4$ | $R_5$ |
|---|---|---|---|---|---|---|
| 1 | I | H | $CH_3CO$ | $C_{17}H_{31}CO$ | H | H |
| 2 | I | H | $C_4H_7CO$ | $C_{17}H_{31}CO$ | H | H |
| 3 | I | $CH_3CO$ | $C_4H_7CO$ | H | H | H |
| 4 | I | $C_{10}H_{13}CO$ | $C_4H_9CO$ | H | H | H |
| 5 | I | $C_4H_7CO$ | $C_4H_9CO$ | H | H | H |
| 6 | I | $CH_3CO$ | $C_9H_{19}CO$ | H | H | H |
| 7 | I | $C_4H_9CO$ | $C_{11}H_{23}CO$ | H | H | H |
| 8 | I | $C_{13}H_{27}CO$ | $CH_3CO$ | H | H | H |
| 9 | I | H | H | H | H | H |
| 10 | I | H | $CH_3CO$ | H | H | H |
| 11 | I | $CH_3CO$ | $CH_3CO$ | $CH_3CO$ | H | H |
| 12 | I | $C_6H_5CO$ | $C_6H_5CO$ | $C_6H_5CO$ | H | H |
| 13 | I | $CH_3CO$ | $CH_3CO$ | $C_{17}H_{31}CO$ | H | H |
| 14 | I | $C_{13}H_{27}CO$ | $CH_3CO$ | $CH_3CO$ | H | H |
| 15 | I* | $CH_3CO$ | $CH_3CO$ | $CH_3CO$ | H | H |
| 16 | I | $CH_3CO$ | $CH_3CO$ | $CH_3CO$ | H | $CH_3$ |
| 17 | I | $CH_3CO$ | $CH_3CO$ | $CH_3CO$ | $CH_3CO$ | $CH_3CO$ |
| 18 | II | — | $CH_3CO$ | $C_{17}H_{31}CO$ | H | H |
| 19 | III | H | H | H | — | OH |
| 20 | III | H | H | H | — | H |
| 21 | III | $CH_3CO$ | $CH_3CO$ | $CH_3CO$ | — | OH |
| 22 | III | $C_3H_7CO$ | $C_3H_7CO$ | $C_3H_7CO$ | — | OH |
| 23 | III | $CH_3CO$ | $CH_3CO$ | $CH_3CO$ | — | $CH_3COO$ |
| 24 | IV | — | — | — | — | — |

I*: 3-Deoxo-3β-hydroxy derivative h) Cells

In the experiments, MT-4 cells were used. The cells were incubated at 37° C. under 5% $CO_2$ in RPMI-1640 medium (FCS, Flow laboratories, North Ryde, Australia) supplemented with 100 μg/mL of streptomycin (Meiji Seika, Tokyo, Japan), and 100 U/mL of penicillin G (Banyu Pharmaceutical, Tokyo, Japan).

i) Virus

HIV-1 was obtained from culture supernatant of MOLT-4 cells that had been persistently infected with LAV-1.

j) Assay of cytopathic effect(CPE) of HIV-1 in MT-4 cells

The inhibitory effect of test compounds on HIV-1-induced cytopathogenicity was measured by the method of Harada, Koyanagi & Yamamoto (1985). MT-4 cells were infected for 1 hour with HIV-1 (at $TCID_{50}$ of 0.001/well) and non-adsorbed virus was removed by washing. Then, the cells were resuspended in RPMI-1640 medium at a concentration of $1.5 \times 10^5$ cells/mL. A 200 μL/well of the cell suspension was cultured for 5 days in days in a 96-well culture plate containing various concentrations (12 doses, maximum 1,000 μg/mL and minimum 0.49 mg/mL) of the test compounds. Control assays were performed in the absence of test compounds with HIV-1-infected and uninfected cultures. On day 5, the $IC_{100}$ of the test compound required for completely preventing HIV-1-induced CPE(IC) was determined through an optical microscope and the cell growth was examined to give the $CC_0$ that reduces the viability of MT-4 cells.

k) Activation of protein kinase C by compounds 1 to 24 PKC activation was assayed by measuring the incorporation of $^{32}P$ radioactivity from [γ-$^{32}P$] ATP into peptide, Arg-Lys-Arg-Thr-Leu-Arg-Arg-Leu-OH, using a Biotrak PKC enzyme assay system code RPN 77 kit except that TPA in the kit was replaced by compounds 1 to 24 (2.7 μg/mL and 10 ng/mL) dissolved in DMSO (final concentration of DMSO not exceeds 0.02%). The reaction mixture contained, in a total volume of 55 μL, 2 milli units PKC, 50 mM Tris/HCl (pH 7.5), 0.13% w/v mercaptoethanol, 2.1 mM EDTA, 4.18 mM EGTA, 20.9 μg/mL phenyl methyl sulfonyl fluoride, 4.2 mM benzamidine, 1.4 nM calcium acetate, 75 mM peptide, 34 μg/mL L-α-phosphatidyl-L-serine, 3.4 mM DTT, 0.68 mM sodium azide, and 6.5 nM MgCl$_2$, etc.

After addition of 0.55 nM [γ-$^{32}$P] ATP (50×10$^3$ cpm/nmol), the reaction mixture was mixed and allowed to be kept at 37° C. for 30 minutes. Then the reactions were terminated by the addition of 10 μl of ice-cold stop reagent. Aliquots of 35 μL were transferred to the center of peptide binding discs. After 10 minutes, the discs were washed two times with 75 mM orthophosphoric acid. The activity of $^{32}$P-labeled samples was counted in 10/mL of a scintillation fluid for 1 minute. In the presence of TPA, lipid and calcium chloride, PKC activation represents 100% and corresponds to 8400 nmol/mg/min (positive control). Values for the activation of PKC by compounds 1 to 24 are given as the mean of duplicate determinations, and calculated relative to that of the positive control. Blank (in the absence of PKC) and control (in the absence of TPA or tested samples) were also carried out. One unit of PKC was defined as that amount of enzyme, which incorporated 1 nmol of phosphate from ATP into its substrate, peptide, per minute under the assay conditions, described above. In the presence of 34 μg/mL L-α-phosphatidyl-L-serine and 2.7 μg/mL TPA, PKC activity was completely inhibited by staurosporine at a concentration of 180 mM.

2. Results and Discussion

Isolation and identification of phorbol esters from *Croton tiglium*

By bioassay directed fractionation of the ether-soluble portion of the methanol extract of the seeds of *Croton tiglium*, 8 kinds of phorbol diesters (compounds 1 to 8) were isolated. Their structures were determined by means of spectroscopic methods such as NMR and MS or by means of GC/MS after selective hydrolysis. Compounds 6 to 8 were identified as 12-O-acetylphorbol-13-decanoate (compound 6), 12-O-(2-methylbutyroyl)phorbol-13-dodecanoate (compound 7), and 12-O-decanoylphorbol-13-acetate (compound 8; TPA) (Hecker, 1971; Hecker, 1974). Compounds 1 to 5 are new and their structures were determined as follows.

Compound 1 (API-MS, m/z 691[M+Na]$^+$) showed absorption bands in the IR($v_{max}$ 1650 cm$^{-1}$) and UV spectra ($\lambda_{max}$ 243 nm), which indicated presence of α,β-conjugated C=O in the molecule. $^1$H—$^1$H COSY and HMQC measurement experiments were conducted and $^1$H and $^{13}$C NMR spectra were analyzed, which showed patterns similar to those of compounds 6 to 8, with signals at δ7.58 for H-1 (C-1 at δ160.4), 1.78 for H-19 (C-19 at δ10.1), and 208.7 for C-13. Signals for two ester carbonyls were also seen at δ174.0 and δ173.5. The downfield shift of C-13 (δ68.0) and C-20 (δ69.2; H$_2$-20 at δ$_H$ 4.46) suggested acylation at the two carbons. Long-range correlations observed in the HMBC spectrum of compound 1 between H$_2$-20 and a carbonyl carbon signal at δ173.5 confirmed acylation at C-20 with an octadecadienoyl group. The 9Z,12Z configuration of this residue was evident from the $^{13}$C NMR spectrum [CH$_2$—CH=CH—CH$_2$—CH=CH—CH$_2$ appeared at δ27.2]. Furthermore, hydrolysis of compound 1 with HClO$_4$ gave two products. The first product was identified as a monoester, 10 (m/z 406[M]$^+$), H$_2$-20 at δ4.00) and the second product was, after methylation, identified as 9Z,12Z-octadecadienoic acid methyl ester by GC/MS (t$_R$ 19.25 min, m/z 294[M]$^+$). The chemical shift of H-1, H-7 (δ5.70), H-8 (δ3.20) and H-10 (δ3.14) are diagnostic of the A/B trans-ring junction (Sakata, Kawazu & Mitsui, 1971; Ronlan & Wickbeg, 1970). Furthermore, the present inventors observed NOESY correlations of H-1 with H-10, H-18 (δ1.04) and H-19 (δ1,78), and those of H$_2$-5 (δ2.52 and 2.38) with H-8, which led us to conclude the structure of compound 1 as to be 13-O-acetylphorbol-20-(9Z,12Z-octadecadienoate).

Compound 2 (API-MS, m/z 731[M+Na]$^+$) provided spectral data quite similar to that of compound 1. However, signals for an acetyl group in compound 1 were replaced by signals for a tigloyl group in compound2 [δ$_H$ 6.87 (δ138.7, C(CH$_3$)=CH—), 128.1 (s, C=CH), 1.80 and 1.82 (δ14.5 and 10.1, 2×CH$_3$)]. The HMBC spectrum indicated the acylation at C-13 with a tigloyl group. The 9Z,12Z-octadecadienoyl group (identified by GC/MS after selective hydrolysis with HClO$_4$ followed by methylation) was assigned to C-20. Thus, the structure of compound 2 was established to be 13-O-tigloylphorbol-20-(9Z,12Z-octadecadienoate).

By the analysis of NMR and MS data of compound 3 (EI-MS, m/z 488 [M]$^+$ and fragment ions at 428 and 389), the compound was expected to be a phorbol-12,13-diester possessing two acyl groups with molecular weights of 59 and 99 (as indicated in "Experiments"). On the basis of HMBC and GC/MS, an acetyl group was assigned to C-12 (δ$_H$ 5.43/δ$_c$ 76.6), and a tigloyl group [a methane proton signal at δ6.85 for C(CH$_3$)=CH, rather than at δ6.15 in its isomer, angeloyl group] (Evans et al., 1978) to C-13 (δ$_c$ 65.7). Thus, compound 3 was established as a new phorbol diester, 12-O-acetylphorbol-13-tigliate.

Most of the spectral data of compound 4 (EI-MS, m/z 602 [M]$^+$) were similar to those of compound 6 except that the signals of an acetyl group in compound 6 were replaced by signals for a 2-methylbutyryl group in compound 4. Selective hydrolysis with 0.1M KOH/MeOH gave 2-methylbutyricacid methylester,which was identified by GC/MS (t$_R$ 9.40 min, m/z 116 [M]$^+$) and confirmed the bonding of 2-methylbutyryl group at C-13. Similarly, a decanoyl group was assigned to C-13 after hydrolysis with 0.2 M NaOMe and GC/MS (decanoic acid methyl ester at t$_R$ 10.16 min, m/z 186 [M]$^+$). The structure of compound 4 was determined to be 12-O-decanoylphorbol-13-(2-methylbutyrate), a new positional isomer of a compound obtained previously from the plant under investigation (Evans et al., 1983; Hecker et al, 1974).

When compared with those of compound 4, the C-12 in compound 5 (EI-MS, m/z 530 [M]$^+$) was occupied by a tigloyl group instead of a decanoyl group. Assignment of the position of acylation undertaken on the basis of HMBC and GC/MS experiments confirmed that compound 5 as 12-O-tigloylphorbol-13-(2-methylbutyrate), a new positional isomer of the compound isolated previously from *Euphorbia frankiana* Berger and *E. coerulescens* Haw (Evans et al., 1983; Hecker et al., 1974).

b) Preparation of phorbol ester related compounds

Hydrolysis of Fr. 18–20 with Ba(OH)$_2$/MeOH (Cairnes, Mirvish, Wallcave, Nagel & Smith, 1981; Mishra, Estensen & Abdel-Monem, 1986) yielded tetracyclic diterpenes, phorbol (compound 9), 4α-phorbol (or isophorbol) (compound 19), and 4-deoxy-4α-phorbol (compound20), identified by comparison of their spectral data (see "Experiments") with that reported in the literature (Hecker, 1966; Tseng, Van Duuren & Solomon, 1977; Evans & Kinghorn, 1973; Hecker, Bartsch, Gschwent, Harle, Kreibich, Kubinyi et al., 1967). Phorbol derivatives (compounds 11 and 12) were synthesized from compound 9, while compounds 15 to 17 were synthesized from compound 11 (Bartsch, Snatzke & Hecker, 1968; Hecker, Szczepanski, Kubinyi, Bresch, Harle, Schaireret al., 1966; Hecker, Kubinyi, Szczepanski, Harle & Bresch, 1965; Crombie, Games & Pointer, 1968; Zayed, Sorg & Hecker, 1984), and compounds 21–23 were synthesized from compound 19 (Hecker, Harle, Schairer, Jaboci, Hoppe, Gassmann et al., 1968). Reaction of compound 1 with mesyl chloride in pyridine at room temperature afforded compound 18 (Bartsch & Hecker, 1969), while compound 24 was obtained from compound 21 after irradiation with UV light at 254 nm (Hecker et al., 1968).

c) Inhibition of HIV-1-induced cytopathic effect (CPE) in MT-4 cells by compounds 1–24

A variety of phorbol esters and related compounds were tested for their ability to inhibit the replication and infectivity of HIV-1 in MT-4 cells, a human CD4-positive cell line continually infected with HTLV-1, and the results are presented in Table 3.

Table 3: Inhibition of HIV-1-induced cytopathic effect (CPE) and activation of PKC by various phorbol derivatives

| | Anti-HIV-1 ($\mu$g/mL) | | | % Activity of PKC at Various Concentrations | |
|---|---|---|---|---|---|
| No. | $IC_{100}$ | $CC_0$ | r* | 10 ng/mL | 2.7 $\mu$g/mL |
| 1 | 15.6 | 62.5 | 4.01 | 0 | 32 |
| 2 | 7.81 | 62.5 | 8.00 | 14 | 32 |
| 3 | 125 | 500 | 4.00 | 16 | 30 |
| 4 | 7.81 | 31.3 | 4.01 | 0 | 0 |
| 5 | 31.3 | 62.5 | 2.00 | 10 | 40 |
| 6 | 0.0076 | 62.5 | 8220 | 0** | 17 |
| 7 | 15.6 | 62.5 | 4.01 | 16 | 30 |
| 8 | 0.00048 | 31.3 | 65200 | 96 | 98 |
| 9 | NE | 1000 | — | 8 | 39 |
| 10 | 125 | >1000 | >8.00 | 0 | 14 |
| 11 | 62.5 | 125 | 2.00 | 0 | 15 |
| 12 | NE | 31.3 | — | NT | 100 |
| 13 | 7.81 | 62.5 | 8.00 | 0 | 44 |
| 14 | 15.6 | 62.5 | 4.01 | 0 | 30 |
| 15 | 500 | 1000 | 2.00 | 0 | 26 |
| 16 | 31.3 | 125 | 3.99 | 0 | 0 |
| 17 | 125 | 250 | 2.00 | 0 | 26 |
| 18 | 7.81 | 125 | 16.0 | 24 | 24 |
| 19 | NE | 500 | — | 1 | 5 |
| 20 | NE | 500 | — | 0 | 25 |
| 21 | 250 | 500 | 2.00 | 0 | 39 |
| 22 | NE | 62.5 | — | 0 | 0 |
| 23 | NE | NT | — | 0 | 60 |
| 24 | NE | 500 | — | 0 | 93 |

*r = $CC_0/IC_{100}$
**No activation of PKC was observed at 100 ng/mL.
NE: Not effective.
NT: Not tested.

The most potent compounds, 8 and 6, had complete inhibition of CPE at concentrations ($IC_{100}$) of 0.48 and 7.6 ng/mL, with minimum cytotoxic concentrations ($CC_0$) of 31.3 and 62.5 $\mu$g/mL, respectively. Next in potency were compounds 2, 4, 13 and 18 ($IC_{100}$: 7.8 $\mu$g/mL; $CC_0$: 62.5, 31.3, 125 $\mu$g/mL). Then, compounds 1, 7, and 14 all showed $IC_{100}$ values of 15.6 $\mu$g/mL, respectively. Compounds 5 and 16 showed complete inhibition of CPE at concentrations of 31.3 $\mu$g/mL, while compounds 3, 10, 11, and 17 were observed effective at concentrations of 62.5 to 125 $\mu$g/mL. Compounds 9, 12, 19, 20, 22, and 24 did not show anti-HIV-1 activity at concentrations up to 500 $\mu$g/mL.

d) Activation of PKC by compounds 1 to 24

Under the conditions where PKC from mouse brain was activated by calcium, phosphatidylserine and TPA, the effects of compounds 1 to 24 on PKC were investigated at a standard concentration of 10 ng/mL and at a higher concentration of 2.7 $\mu$g/mL (Table 3). TPA (compound 8) showed almost 100% activation of PKC at both concentrations. Lumiphorbol-12, 13, 20-triacetate (compound 24) activated PKC by 93% at high concentrations, while no activation was observed at the standard concentration. Compounds 4, 16, and 22 showed no activation at concentrations in a range of 10 ng to 2.7 $\mu$g/mL. Compound 6 having potent anti-HIV activity showed no activation at 10 to 100 ng/mL but activated it by 17% at the higher concentration. Other compounds, such as compounds 1, 10, 11, 13 to 15, 17, 19 to 21, and 23 did not activate PKC at 10 ng/mL, but appreciably activated it by 5 to 60% at 2.7 $\mu$g/mL.

e) Structure-Activity Relationship

In an attempt to correlate activities on structural basis, the activities of the phorbol esters (compounds 1 to 8) presently isolated and several of their derivatives were assessed for the anti-HIV-1 activity and for the activation of PKC. All CPE inhibition-active phorbol derivatives (compounds 1 to 8, 13, 14, 16, and 18) were of A/B trans configuration. On the other hand, the A/B cis analogs (compounds 19 to 24) had no remarkable inhibitory effect on CPE. No remarkable PKC activation was observed at standard measurement concentration (10 ng/mL) except for TPA. Esterified forms (compounds 21 and 23) and compound 24 synthesized by the intramolecular cycloaddition of compound 21 showed enhanced activation of PKC at high concentrations. Apart from the A/B ring configuration, the most active compounds were phorbol 12,13- or 13,20-diesters possessing long-chain and short-chain acyl groups (long chain at C-12 as in compounds 4 and 8, at C-13 as in compound 6, or at c-20 as in compounds 1 and 2). In this case, the 12,13-diesters were more active. Diesters possessing two short residues (compounds 3 and 5) showed weak inhibitory effects against CPE and weak activation of PKC. TPA (compound 8, possessing a tetradecanoyl group and an acetyl group) was equipotent, while compound 6 did not activate PKC at concentrations in a range of 10 to 100 ng/mL. Only 17% activation was observed at a concentration of 2.7 $\mu$g/mL, which is 346-fold higher than its $IC_{100}$ (7.6 ng/mL). Compound 4 (possessing a decanoyl group and a methylbutyroyl residue) completely inhibited CPE at 7.81 $\mu$g/mL, but did not show any activation of PKC. This suggested that the difference in chain lengths of acyl groups and its relative positions significantly influenced both activities.

The long chain acyl group (for example, a tetradecanoyl group) is an essential requirement for potent CPE inhibitory effect. For PKC, similar tendency has been observed as in compound 8. Whereas, another long chain acyl group (for example, a decanoyl group) bonded to C-12 (with a methylbutyryl residue at C-13 as in compound 4, or an acetyl group at C-13 as in compound 6) were found to be essential for the anti-HIV activity of these compounds, but not for the activation of PKC. Enhancement of the anti-HIV activity of compound 1 was observed after acetylation of HO-12 without an increase in the activity of PKC (as in compound 13). The CPE inhibitory activity of compound 18, which was obtained by homoallylic rearrangement of the α-(acetoxycyclopropyl)carbinol group of compound 1, was enhanced 2 times. This suggested the group is not a critical requirement for the inhibitory activity. Compound 14, obtained by introducing an acetyl group to the C-20 of TPA (compound 8), the both activities were dramatically decreased. Removal of the long chain acyl group from compound 8 resulted in a decrease the both activities. On the other hand, phorbol alcohols (compounds 9, 19, and 20) did not show CPE inhibitory effect but were weak activators of PKC. In the case of phorbol triesters (compounds 11 to 16), activities were variable. Addition of acetyl group(s) to compound 9 enhanced the CPE inhibitory effect. Reduction of a carbonyl group at C-3 in compound 11 led to compound 15, which showed loss of CPE inhibitory effect, suggesting participation of the carbonyl group in the inhibitory effect.

As compared with compound 11, compound 16, whose HO-4 has been methylated, showed no activation of PKC but shoed an increased in the CPE inhibitory effect. On the other hand, as observed in compound 17, acetylation of HO-4 and HO-9 seems to have no particular importance. Benzoylation of compound 9 enhanced the activation of PKC as in compound 12.

Phorbol esters and related compounds have been reported to exert a remarkable range of biochemical effects and a number of structure-activity studies in various systems have been reported (Evans et al., 1983; Evans et al., 1978; Def Chaffoy de Courcelles et al., 1984; Hecker, 1978; Blumberg, 1980; Blumberg, 1981; Blumberg, 1988; Kupchan et al., 1976; Gustafson et al., 1992; Gschwendt et al., 1974; Erickson, Beutler, Cardellina-II, McMahan, Newman & Boyd, 1995; Handa, Kinghom, Cordell & Farnsworth, 1983).

The structure-activity findings of phorbol esters as described above are summarized as follows:

That is, The A/B trans configuration and the 12,13- or 13,20-diacyls were essential for activities. This is indicated by the loss of activity in most of the A/B cis-analogs. The lengths and- the relative positions of acyl groups had variable effects on the activity. Thus, cyclopropyl-carbinol group was not essential for the activity of compound. The CPE inhibitory effect of the compounds is sharply reduced or eliminated by reduction of the carbonyl group, by further esterification or by alkaline hydrolysis of the active compound. Methylation of HO-4 enhanced the CPE inhibitory effect and led to a decrease in PKC activation.

f) Selection of preferable antiviral agents

As evaluation standards for selecting preferable antiviral agents from various phorbol derivatives, the present inventors selected the following two standards:

(1) A ratio $r=CC_0/IC_{100}$, i.e., ratio of concentration $CC_0$ at which survival of MT-4 cells is decreased upon cell proliferation tests to concentration $IC_{100}$ at which HIV-1-induced cytopathic effect (CPE) on MT-4 cells is inhibited by 100%, is 2 or more and (2) A protein kinase C(PKC) activation of 30% or less at a concentration of 10 ng/mL.

Out of the phorbol derivatives described in Table 3, the evaluation standard (1) eliminates phorbol derivatives, compounds 9, 12, 19, 20, 22, 23, and 24 (all of these showed no effect) while other phorbol derivatives had r of 2 or ore. Although phorbol derivatives, compounds 6 and 8, had very large r values but the evaluation standard (2) eliminates compound 8 since it has a strong carcinogenicity promoting effect.

As stated above, considering totally, among the phorbol derivatives described in Table 3, the phorbol derivative, compound 6, revealed to be the most excellent antiviral agent.

It is preferred that further evaluation standards be adopted as needed so that optimal antiviral agents can be selected.

The antiviral agent of the present invention has higher antiviral effects against virus, typically HIV-1 virus, and less deleterious side effects and therefore is useful as an anti-HIV medicine.

Further, the phorbol derivatives of the present invention are novel compounds, which can serve as active ingredient of the antiviral agent of the present invention and can give suggestion on the development of antiviral agents having both high activity and safety on the aspects of chemical structure and pharmacological activity as well as safety.

What is claimed is:

1. An antiviral agent comprising as an active ingredient a phorbol derivative of formula (I):

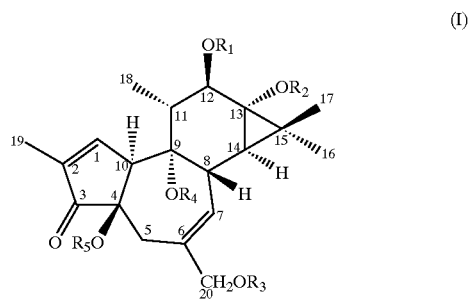

(wherein $R_1$, $R_2$, $R_3$, $R_4$, and $R_5$, independently one another, represent a hydrogen atom, an aliphatic carboxylic acid residue, or an aromatic carboxylic acid residue)

having a ratio $r=CC_0/IC_{100}$, i.e., ratio of concentration $CC_0$ at which survival of MT-4 cells is decreased upon cell proliferation tests to concentration $IC_{100}$ at which HIV-1-induced cytopathic effect (CPE) on MT-4 cells is inhibited by 100%, of 2 or more and having a protein kinase C(PKC) activation of 30% or less at a concentration of 10 ng/mL.

2. An antiviral agent comprising as an active ingredient a phorbol derivative of formula (II):

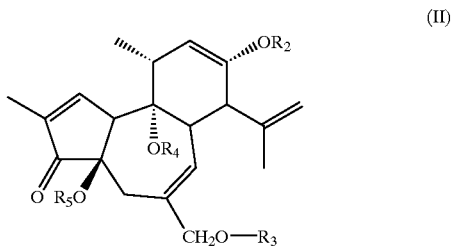

(wherein $R_1$, $R_2$, $R_3$, $R_4$, and $R_5$, independently one another, represent a hydrogen atom, an aliphatic carboxylic acid residue, or an aromatic carboxylic acid residue)

having a ratio $r=CC_0/IC_{100}$, i.e., ratio of concentration $CC_0$ at which survival of MT-4 cells is decreased upon cell proliferation tests to concentration $IC_{100}$ at which HIV-1-induced cytopathic effect(CPE) on MT-4 cells is inhibited by 100%, of 2 or more and having a protein kinase C(PKC) activation of 30% or less at a concentration of 10 ng/mL.

3. A phorbol derivative of formula (I):

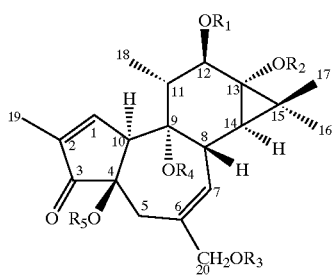

(wherein $R_1$, $R_4$, and $R_5$ represent each a hydrogen atom, $R_2$ represents an acetyl group, $R_3$ represents a linoleic acid residue, or $R_1$, $R_4$, and $R_5$ represent each a hydrogen atom, $R_2$ represents a tigloyl group, $R_3$ represents a linoleic acid residue, or $R_1$ represents an acetyl group, $R_2$ represents a tigloyl group, $R_3$, $R_4$, and $R_5$ represent each a hydrogen atom, or $R_1$ represents a decanoyl group, $R_2$ represents a 2-methyllactic acid residue, $R_3$, $R_4$, and $R_5$ represent each a hydrogen atom, or $R_1$ represents a tigloyl group, $R_2$ represents a decanoyl group, $R_3$, $R_4$, and $R_5$ represent each a hydrogen atom).

* * * * *

UNITED STATES PATENT AND TRADEMARK OFFICE
CERTIFICATE OF CORRECTION

PATENT NO.    : 6,268,395 B1
DATED         : July 31, 2001
INVENTOR(S)   : Masao Hattori It is certified that error appears in the above-identified patent and that said Letters Patent is hereby corrected as shown below:

<u>Title page,</u>
Item [30], Foreign Application Priority Data,
Change "Nov. 11, 1999 (JP) 11-320867" to -- Nov. 11, 1999 (JP) 11-320967 --

Signed and Sealed this

Twenty-sixth Day of February, 2002

Attest:

JAMES E. ROGAN
*Attesting Officer*                *Director of the United States Patent and Trademark Office*